United States Patent [19]
Omet

[11] Patent Number: 4,564,292
[45] Date of Patent: Jan. 14, 1986

[54] REFRACTOMETER

[75] Inventor: Reinhard Omet, Babenhausen, Fed. Rep. of Germany

[73] Assignee: Phoenix Artmaturen-Werke Bregel GmbH, Frankfurt, Fed. Rep. of Germany

[21] Appl. No.: 614,722

[22] Filed: May 25, 1984

[30] Foreign Application Priority Data

Jun. 11, 1983 [DE] Fed. Rep. of Germany ....... 3321203

[51] Int. Cl.$^4$ ............................................. G01N 21/41
[52] U.S. Cl. .................................... 356/133; 356/243; 356/246
[58] Field of Search ............... 356/128, 130, 133, 135, 356/136, 137, 243, 246; 250/573, 575, 576, 577

[56] References Cited

U.S. PATENT DOCUMENTS

| 3,282,149 | 11/1966 | Shaw et al. | 356/130 |
| 3,520,619 | 7/1970 | Ward | 356/133 |
| 3,917,410 | 11/1975 | Ulrich | 356/133 |
| 4,152,075 | 5/1979 | Rellstab et al. | 250/227 |
| 4,354,180 | 10/1982 | Harding | 250/577 |

FOREIGN PATENT DOCUMENTS 2137842 11/1981 Fed. Rep. of Germany .

Primary Examiner—F. L. Evans
Attorney, Agent, or Firm—Michael J. Striker

[57] ABSTRACT

A refractometer for measuring the index of refraction of a sample medium comprises a sample medium sensor and a reference medium sensor. Both sensors are combined into a single measuring probe which is connected by a flexible cable to a housing unit which accommodates the source of light, photodetectors, the test data processor and the indicator. The refractometer with the single probe is portable and easy to handle.

5 Claims, 2 Drawing Figures

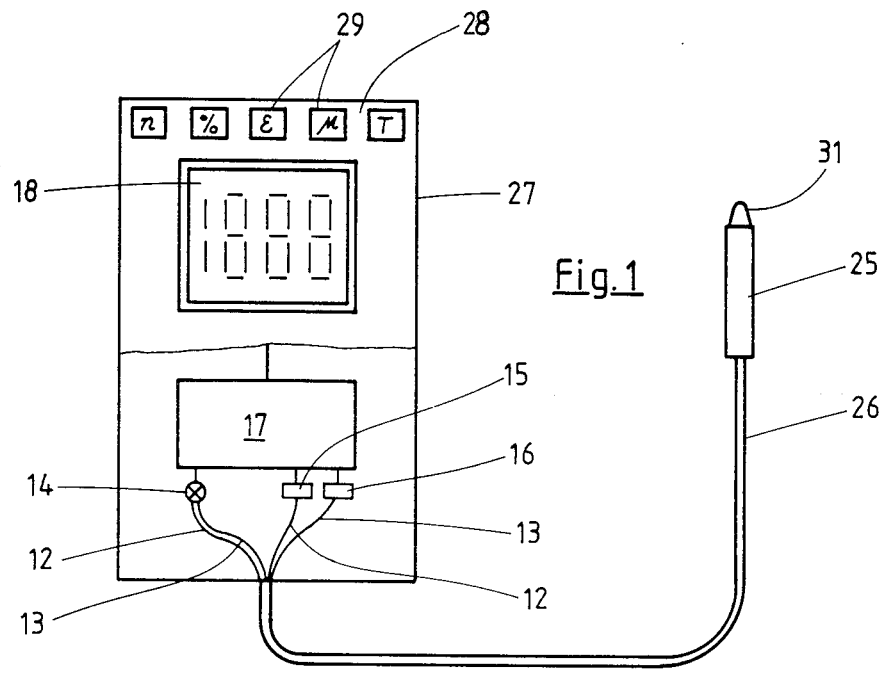
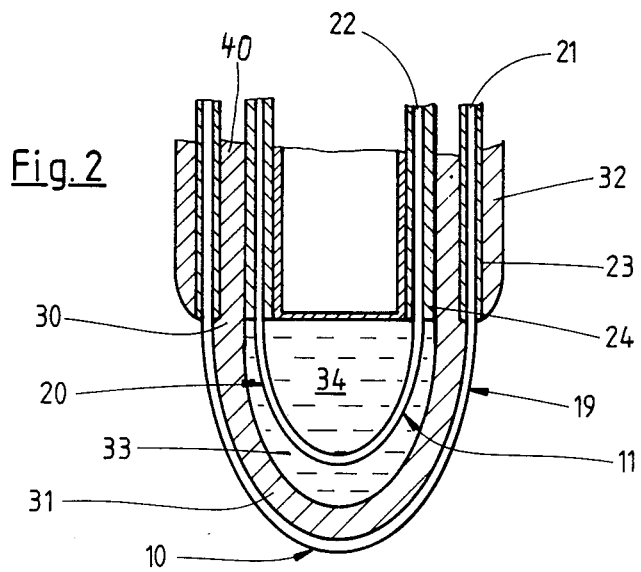

REFRACTOMETER

BACKGROUND OF THE INVENTION

The present invention relates to a refractometer for measuring the index of refraction of a sample medium by measuring the transmission of light through a sensor, which transmission is a substantially linear function of the index of refraction.

Known refractometers normally serve the purpose of measuring the index of refraction of a fluid. Refractometers of the type under discussion have been known in the art and have been disclosed, for example in the German Pat. No. 2,137,842 or U.S. Pat. No. 3,282,149. Inasmuch as the index of refraction of the sample medium depends upon the temperature a so-called reference sensor for eliminating the temperature influence has been employed, which has been surrounded with the reference medium. The outlet value of the reference sensor with the known refractive index is inversely proportional to the temperature of the sample medium or of the environment. The temperature influence can be eliminated from the output value of the sample medium sensor in the test data processing device and is normalized relative to the temperature in the indicator device. That is, the refractive index of the sample medium referred to the ambient temperature is indicated on the indicator.

In known refractometers the sample medium sensor and the reference medium sensor are separated from each other for measuring the index of refraction of a fluid. The sensors are arranged in two separate vessels having the same temperature; the vessels are respectively filled with the probe for the reference medium and the probe for the sample medium. Such a refractometer is bulky, and is unsuitable or difficult in handling and for a mobile use.

SUMMARY OF THE INVENTION

It is an object of the present invention to provide an improved refractometer.

It is another object of the present invention to provide a portable refractometer which is easy to handle, which can be carried by an operator without any difficulties and which can be applied at any even constantly changed locations and in various environments.

These and other objects of this invention are attained by a refractometer for measuring the index of refraction of a sample medium, comprising a source of light; a sample medium sensor surrounded by a sample medium, a first light conductor coupling said sample medium sensor to the source of light, so that the light from said source is directed along said sample medium sensor, said first light conductor having a substantially U-shaped, curved unscreened portion which forms said sample medium sensor, first photodetection means connected to said first light conductor for measuring the transmitted radiant energy passed through said sample medium sensor; a reference medium sensor surrounded by a reference medium; a second light conductor coupling said reference medium sensor to said source of light; second photodetection means connected to said second light conductor for measuring the transmitted radiant energy passed through said reference medium sensor; test data processing means for measuring the difference in light transmitted by each sensor; indicator means for indicating the index of refraction in accordance with said difference, said sample medium sensor and said reference medium sensor being combined into a single measuring probe; a housing accommodating said source of light, said first and second photodetection means, said test data processing means and said indicator means; and cable means connecting said single probe to said housing, said probe including an elongated probe member, a casing surrounding said probe member, and a measuring tip having in the direction of elongation of the probe a substantially U-shaped cross-section and extended outwardly from said casing, said measuring tip having an outer surface carrying thereon said sample medium sensor, said measuring tip being formed with an internal hollow space filled with the reference medium, said reference medium sensor being positioned in said hollow space.

The refractometer according to the invention is a truly portable device because it includes only the single measuring probe which is connected to the manageable housing by a flexible cable. The measuring probe should be merely immersed in the sample medium. The removal of the probe out from the sample medium is no longer required. Due to a direct immersion of the measuring probe in the sample medium current changes in the refractive index of the sample medium can be determined and monitored immediately during the running production process. The measurements of the measuring probe being made can be extremely small so that the measuring probe can be immersed even in a reactive glass. The refractometer according to the invention is suitable for laboratory technique and also for analysis technique.

Since many physical and specifically molecular values are in physical connection with the index of refraction the portable refractometer according to the invention can be employed for measuring of a number of various measure values. In order to avoid a complicated practice of converting tables all the necessary conversions are performed electronically in the test data processing device. The indication of the desired measured values can be determined by selection on the keyboard provided on the front panel of the housing.

Inasmuch as the portable refractometer according to the invention determines all the measured values by means of light measurements the utilization of the refractometer is not limited to certain places depending on the environment conditions. Measurements can be carried out by means of the portable refractometer of this invention in high temperature field, electrical field, under high voltage and also in explosive and aggressive environments.

The second light conductor may have a substantailly U-shaped, curved unscreened portion which forms said reference medium sensor.

The reference medium sensor may extend substantially parallel to the sample medium sensor.

The first and second light conductors may be flexible light conducting fibers.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 1 is a schematic illustration of the portable refractometer according to the invention; and FIG. 2 is a partial sectional view through a measuring probe of the refractometer of FIG. 1, on the enlarged scale.

DETAILED DESCRIPTION OF THE PREFERRED EMBODIMENT

Referring now to the drawings in detail the reference numeral 10 designates a sample medium sensor and the reference numeral 11 denotes a reference medium sensor of the refractometer. Sensors 10 and 11 are respectively connected to light conduits 12 and 13 which in turn are interconnected between a common light source 14 and respective photodetectors 15 and 16. The photodetectors 15 and 16 schematically shown in FIG. 1 are connected to a test data processing device 17 which in turn is coupled to an indicator denoted by reference character 18.

It should be noted that the constructions of photodetectors, light source, test data processing device and indicator device as well as the materials for the sensors and the method of measuring the index of refraction of a sample medium by means of a photoelectric refractometer have been known in the art and are disclosed, for example in U.S. Pat. No. 3,282,149, the entire disclosure of which is incorporated herein by reference. The light passing from the light source 14 to light conductors 12, 13 is partially or totally reflected in sensors 10 and 11 in the known manner, that is the amount of reflected light depends on the ratio of relative light outputs, and thus indexes of refraction are sensed by the sensors surrounded by the reference medium and the medium to be sampled, respectively. The amount of reflected light is measured in the known manner by photodetectors 15, 16. The output signals of photodetectors 15, 16 are delivered to the test data processing device 17 which will determine an indication value for an indicator 18.

As has been known each sensor 10 or 11 can be formed as a single piece with or integral with respective light conducting member 12 and 13. Such a combined construction of each sensor includes a somewhat U-shaped curved portion 19 or 20, each of which merges into respective light conductor 12, 13 at the transition portion. The light conductors 12, 13 are preferably formed as light conducting fibers 21, 22 which are screened by means of screens or sleeves 23, 24, respectively.

The sample medium sensor 10 and the reference medium sensor 11 are combined into a measuring probe 25, which via the light conductors 12, 13 or light conducting fibers 23, 24 enclosed by a flexible cable 26 is connected to a housing 27. The housing 27 accommodates the light source 14, photodetectors 15, 16, the test data processing device 17 and the indicator 18. Furthermore, a keyboard 28 with a plurality of selective keys 29 is provided on the housing 27. A desired measuring value is selected by means of selective keys, in accordance with the index of refraction of the medium being sampled. This selected value is calculated in the known fashion in the test data processing device from the output signals received from the photodetectors 15 and 16 and supplied to the indicator 18 on which this value is released.

In order to spatially and most advantageously combine the sample medium sensor 10 and the sensor for a reference medium 11 the measuring probe 25 includes a probe member 30 having a substantially cylindrical portion 40 and a measuring tip 31 which has in the direction of elongation thereof a somewhat U-shaped cross-section. The probe member 30 is surrounded with an enclosure or casing 32, from which the measuring tip 31, which is not covered with the casing, is outwardly extends. Sample medium sensor 10 is formed by the U-shaped curved portion of the light-conducting fiber 21 and arranged so that the inner surface of sensor 10 abuts against the outer surface of the probe member measuring tip 31. In the interior of the measuring tip 31 a hollow space 33 is provided, which forms a chamber filled with the reference medium 34, preferably fluid. Reference medium sensor 11 is arranged in that chamber and is surrounded in the known fashion with the reference medium. The hollow space 33 is spaced from the outer surface of measuring tip 31 at the smallest possible distance so that a compensation for temperature differences between the outer surface of measuring tip 31 and the reference medium 34 would be made possible in a shortest period of time. The light conductors 12, 13 formed as screened light conducting fibers 21, 22 extend parallel to each other within the cylindrical portion of probe member 30 and then merge into the flexible cable 26.

The present invention is not limited to the above identified embodiment of the invention. The reference medium sensor may be formed by a spirally coiled bar similarly to that described in the aforementioned U.S. Pat. No. 3,282,149.

The aforedescribed refractometer is not limited to measuring of the indexes of refraction of fluids. It can be as well utilized for measuring the indexes of refraction of gases or solids. In the case of testing gaseous media the index of refraction must be taken into consideration depending on gas pressure, while in the instance of solids such solids are tested in which the measuring probe 25 with the measuring tip 31 can be compressed.

Probe 25 is immersible in the medium to be sampled.

It will be understood that each of the elements described above, or two or more together, may also find a useful application in other types of photoelectric refractometers differing from the types described above.

While the invention has been illustrated and described as embodied in a photoelectric refractometer, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a refractometer for measuring the index of refraction of a sample medium, comprising a source of light; a sample medium sensor surrounded by a sample medium, a first light conductor coupling said sample medium sensor to the source of light so that the light from said source is directed along said sample medium sensor, said first light conductor having a substantially U-shaped curved unscreened portion which forms said sample medium sensor, first photodetection means connected to said first light conductor for measuring the transmitted radiant energy passed through said sample medium sensor; a reference medium sensor surrounded by a reference medium; a second light conductor coupling said reference medium sensor to said source of light; second photodetection means connected to said second light conductor for measuring the transmitted radiant energy passed through said reference medium sensor; test data processing means for measuring the difference in light transmitted by each sensor; and indicator means for indicating the index of refraction in accordance with said difference, the improvement comprising a single measuring probe, said sample medium sensor and said reference medium sensor being combined into said single measuring probe; a housing accommodating said source of light, said first and second photodetection means, said test data processing means and said indicator means; and cable means connecting said single probe to said housing, said probe including an elongated probe member, a casing surrounding said probe member, and a measuring tip having in the direction of elongation of the probe a substantially U-shaped cross-section and extended outwardly from said casing, said measuring tip having an outer surface carrying thereon said sample medium sensor, said measuring tip being formed with an internal hollow space filled with the reference medium, said reference medium sensor being positioned in said hollow space.

2. The refractometer as defined in claim 1, wherein said second light conductor has a substantially U-shaped, curved unscreened portion which forms said reference medium sensor.

3. The refractometer as defined in claim 2, wherein the reference medium sensor extends substantially parallel to the sample medium sensor.

4. The refractometer as defined in claim 3, wherein said first and second light conductors are flexible light conducting fibers.

5. The refractometer as defined in claim 4, wherein said light conducting fibers are screened.

* * * * *